US009227084B2

(12) United States Patent
Isham et al.

(10) Patent No.: US 9,227,084 B2
(45) Date of Patent: Jan. 5, 2016

(54) UNIVERSAL BALLOON FOR BRACHYTHERAPY APPLICATOR

(71) Applicant: RadiaDyne, LLC, Houston, TX (US)

(72) Inventors: John Isham, Houston, TX (US); Christen Springs, Chicopee, MA (US); Stephen J. Wiater, Chicopee, MA (US); Adam Epstein, Chicopee, MA (US)

(73) Assignee: RadiaDyne LLC, Houston, TX (US)

( * ) Notice: Subject to any disclaimer, the term of this patent is extended or adjusted under 35 U.S.C. 154(b) by 400 days.

(21) Appl. No.: 13/624,342

(22) Filed: Sep. 21, 2012

(65) Prior Publication Data

US 2013/0085315 A1    Apr. 4, 2013

Related U.S. Application Data

(60) Provisional application No. 61/540,962, filed on Sep. 29, 2011.

(51) Int. Cl.
| | |
|---|---|
| *A61M 36/10* | (2006.01) |
| *A61M 25/01* | (2006.01) |
| *A61N 5/10* | (2006.01) |
| *A61M 37/00* | (2006.01) |
| *B23P 17/04* | (2006.01) |
| *A61B 19/00* | (2006.01) |

(52) U.S. Cl.
CPC ............ *A61N 5/1007* (2013.01); *A61N 5/1016* (2013.01); *A61N 5/1071* (2013.01); *A61B 2019/5466* (2013.01); *A61M 37/0069* (2013.01); *A61N 2005/1003* (2013.01); *B23P 17/04* (2013.01); *Y10T 29/4997* (2015.01); *Y10T 156/1002* (2015.01)

(58) Field of Classification Search
CPC .................... A61N 2005/1003; A61N 5/1016; A61N 5/1007
See application file for complete search history.

(56) References Cited

U.S. PATENT DOCUMENTS

| | | | | |
|---|---|---|---|---|
| 5,098,755 | A * | 3/1992 | Tanquary et al. | 428/35.5 |
| 5,899,208 | A * | 5/1999 | Bonadio | 128/897 |
| 7,192,436 | B2 * | 3/2007 | Sing et al. | 606/213 |
| 7,300,399 | B2 * | 11/2007 | Bonadio et al. | 600/208 |
| 7,338,430 | B2 | 3/2008 | Lim et al. | |
| 7,740,623 | B2 * | 6/2010 | Nayak et al. | 604/500 |
| 7,744,626 | B2 * | 6/2010 | Mollenauer et al. | 606/213 |
| 8,080,031 | B2 | 12/2011 | Isham et al. | |
| 2006/0020156 | A1 | 1/2006 | Shukla et al. | |
| 2008/0086083 | A1 | 4/2008 | Towler et al. | |
| 2008/0293994 | A1 | 11/2008 | Francescatti et al. | |
| 2009/0227827 | A1 | 9/2009 | Hausen et al. | |
| 2010/0010287 | A1 | 1/2010 | Lubock et al. | |

(Continued)

*Primary Examiner* — Catherine B Kuhlman
*Assistant Examiner* — Shannon McBride
(74) *Attorney, Agent, or Firm* — Boulware & Valoir (57) ABSTRACT

A brachytherapy balloon system, including a brachytherapy applicator and a brachytherapy balloon, is described. The brachytherapy balloon is shaped and sized to fit a vagina, a rectum or an esophagus and is made of elastomeric polymer and has a cylindrical inner surface defining an interior hollow of diameter D with at least one open end into which a brachytherapy applicator of diameter x<D can fit, and an outer surface. The inner and outer surfaces of the brachytherapy balloon together define an inflatable elongated toroidal shape having a distal and a proximal end. The distal end has a diameter less than x, a valve for inflating the balloon, and a retention ring that prevents the brachytherapy applicator from protruding beyond the retention ring and reproducibly positioning the applicator on every use.

19 Claims, 6 Drawing Sheets

(56) References Cited

U.S. PATENT DOCUMENTS

| | | |
|---|---|---|
| 2010/0048978 A1 | 2/2010 | Sing et al. |
| 2010/0069878 A1 | 3/2010 | Parsai et al. |
| 2010/0145132 A1 | 6/2010 | Isham |
| 2010/0145379 A1* | 6/2010 | Isham .......................... 606/192 |
| 2010/0185173 A1 | 7/2010 | Popowski et al. |
| 2011/0040365 A1* | 2/2011 | Hirszowicz et al. ......... 623/1.11 |
| 2011/0071463 A1* | 3/2011 | Ewers et al. .................... 604/26 |
| 2012/0108881 A1* | 5/2012 | Sing et al. ......................... 600/3 |

* cited by examiner

UNIVERSAL BALLOON FOR BRACHYTHERAPY APPLICATOR

PRIOR RELATED APPLICATIONS

This application claims priority to Ser. No. 61/540,962, filed Sep. 29, 2011, and expressly incorporated by reference herein in its entirety.

FEDERALLY SPONSORED RESEARCH STATEMENT

Not applicable.

JOINT RESEARCH AGREEMENT

Not applicable.

FIELD OF THE INVENTION

The invention relates to brachytherapy balloons, systems and methods for treating cancer.

BACKGROUND OF THE INVENTION

Brachytherapy (from the Greek word brachys, meaning "short-distance"), also known as internal radiotherapy, sealed source radiotherapy, curietherapy or endocurietherapy, is a form of radiotherapy where a radiation source is placed inside or next to the area requiring treatment. Brachytherapy is commonly used as an effective treatment for cervical, prostate, breast, and skin cancer and can also be used to treat tumors in many other body sites.

Different types of brachytherapy can be defined according to (1) the placement of the radiation sources in the target treatment area, (2) the rate or 'intensity' of the irradiation dose delivered to the tumor, and (3) the duration of dose delivery. The two main types of brachytherapy treatment in terms of the placement of the radioactive source are interstitial and contact. In the case of interstitial brachytherapy, the sources are placed directly in the target tissue of the affected site, such as the prostate or breast. Contact brachytherapy involves placement of the radiation source in a space next to the target tissue. This space may be a body cavity (intracavitary brachytherapy) such as the uterus or vagina; a body lumen (intraluminal brachytherapy) such as the trachea or oesophagus; or externally (surface brachytherapy), such as the skin. A radiation source can also be placed in blood vessels (intravascular brachytherapy) for the treatment of coronary in-stent restenosis.

The dose rate of brachytherapy refers to the level or 'intensity' with which the radiation is delivered to the surrounding medium and is expressed in Grays per hour (Gy/h). Low-dose rate (LDR) brachytherapy involves implanting radiation sources that emit radiation at a rate of up to 2 Gy·h−1. Medium-dose rate (MDR) brachytherapy is characterized by a medium rate of dose delivery, ranging between 2 Gy·h−1 to 12 Gy·h−1. High-dose rate (HDR) brachytherapy is when the rate of dose delivery exceeds 12 Gy·h−1, and is commonly used for in tumors of the cervix. Pulsed-dose rate (PDR) brachytherapy involves short pulses of radiation.

Brachytherapy is commonly used in the treatment of early or locally confined cervical cancer and is a standard of care in many countries. Cervical cancer can be treated with LDR, PDR or HDR brachytherapy. The chances of staying free of disease (disease-free survival) and of staying alive (overall survival) are similar for LDR, PDR and HDR treatments. However, a key advantage of HDR treatment is that each dose can be delivered on an outpatient basis with a short administration time, providing greater convenience for many patients. In fact, a 2005 survey by the American Brachytherapy Society (ABS) reported that two-thirds of the responding medical providers performed HDR-VBT, and more than 90% of those providers used a single channel vaginal cylinder as the applicator.

Although a popular treatment modality, one of the difficulties with any kind of HDR brachytherapy is that even small errors in positioning can have serious side effects due to the high doses involved. Using endometrial cancer as an example, we will now demonstrate the scope of the problem.

An ABS panel in 2000 provided specific guidelines for HDR applicator selection, insertion techniques, target volume definition, and dose fractionation, among others. The ABS panel recommended that for HDR-VBT, the largest diameter applicator should be selected to ensure close mucosal apposition and to eliminate "air gaps." The panel also recommended, among other things, that (1) the treatment plan should be optimized to conform to the target volume whenever possible while recognizing the limitations of computer optimization, (2) the anisotropic correction should be included in the dose calculation and the optimization points should be placed at the apex (where the majority of the disease is located) and along the curved portion of the cylinder dome in addition to the lateral vaginal mucosa, (3) the dose prescription point should be clearly specified either at the surface or at a 0.5 cm depth (margin), and (4) the dose should be reported both at the vaginal surface and at the 0.5 cm depth, regardless of the dose prescription point.

The 0.5 cm depth treatment protocol has limitations. The use of the depth specification creates a treatment margin to account for applicator and/or patient motion, ensuring that the disease is covered and biochemical failure is avoided. Unfortunately, a corresponding dose is disadvantageously applied. Ideally, a "surface dose" method would be employed with the dose deposited at the surface of the cylinder. However, such a method has proven inadequate, because although the healthy tissue dose becomes negligible, a less than adequate dose is delivered to the target area.

Although the cylinder is the applicator of choice, it has limitations. It is well established that the 1 mm of tissue surrounding the cylinder is the predominant location of the disease. To deliver an appropriate dose to this area, the treatment device must be in direct contact with the vaginal surface. Any obstruction, such as an air pocket occurring between the treatment device and the mucosa, displaces the mucosa away from the dose, resulting in a cold spot or dose reduction to the target. In addition, the presence of air gaps sometimes moves the applicator within the vagina, so that the clinical target volume (CTV) is disadvantageously no longer equivalent to the planning target volume (PTV).

The standard dose protocol typically assumes no air pockets, and proper applicator location. An air pocket creates separation between applicator and mucosa. The separation can displace the target outside of the dose range. This could lead to all, or a portion, of the target displaced outside of the 0.5 cm prescription.

The effects of air pockets on dose delivery have been well documented in recent medical studies. In one such study, the authors of the study determined that 32% of the patients in their study had an air pocket larger then 2 mm, with the median number of air pockets per patient being one pocket. In another study of 25 patients with daily CT scans during treatment, 20 (80%) had one or more air pockets present in the upper vagina in at least one of their six treatment fractions.

The total number of air pockets found throughout treatment for all 25 patients was 90 pockets (60% of treatments). The result was a disadvantageous average dose reduction of 27%.

Other factors, such as applicator positioning, can also have a clinically significant impact on dose delivery. Improper applicator angle can result in increased toxicity and reduced dose to the target. One medical study investigated the effect of the cylinder tilt on the sensitive structure volumes, and suggested simulation of the applicator position before each fraction.

The ABS recommended in 2000 that single-fraction planning was acceptable as long as the geometry of the implant remained the same for every insertion. However, a paradigm shift is emerging in brachytherapy whereby all treatments are becoming image guided, and all fractions are imaged regardless of the implant type. These findings indicate that scanning only the first fraction of a patient's treatment is insufficient for determining vaginal mucosa conformity to the cylinder throughout the course of treatment. Therefore, the findings indicate that to obtain an accurate and complete geometric dosimetric assessment of the patient's treatment, the patient should be imaged for every treatment fraction.

Thus, it is readily apparent that positioning of the applicator is of critical importance during HDR brachytherapy, in order to maximize its effectiveness and minimize its side effects. Current methodology uses gauze packing, as it is a simple and inexpensive method of positioning the applicator. However inexpensive, neither patients nor practitioners like gauze packing as it is neither comfortable, nor easy to implement and achieve consistent positioning.

Latex balloons have been developed to use in place of the gauze. However, all of the prior art balloons are non-conforming—that is they do not hold their shape when squeezed. Such balloons are an improvement over gauze, but still allow for considerable slop in treatment margins because the balloon is easily deformed under pressure and body cavities are a mobile environment. Further, while latex is inexpensive to mold, it is allergenic and many patients cannot use it.

Other solutions employ rigid intracavitary cylinders, which are certainly conforming. However, these have no capacity to adapt to patient-specific anatomy or motion, and are less than comfortable to use.

Therefore, a need exists to eliminate air pockets during HDR brachytherapy, regardless of which bodily orifice is being treated. A need also exists to eliminate the adverse effect of improper applicator angle during HDR brachytherapy. The ideal solution would allow some amount of flexibility, so that patient anatomy and comfort can be accommodated, but would still be conforming, that is hold its shape under in the constrained environment inside the body. The ideal balloon would also be adaptable for use in other body cavities, such as the rectum or oesophagus, and would be capable of use with either single channel or multi-channel applicators, and thus be of universal applicability in hospital settings, regardless of which type of applicator is available.

SUMMARY OF THE INVENTION

Generally speaking, the invention is a universal brachytherapy balloon that is specially shaped so as to properly position the HDR-brachytherapy applicator inside the body for delivery of radiation. The device could also be used for LDR, MDR and PDR and other forms of brachytherapy. The device described herein provides just such a shape. We use a vaginal balloon herein as an example, but the shape can be varied according to whichever body part is to be treated.

Figure 1:
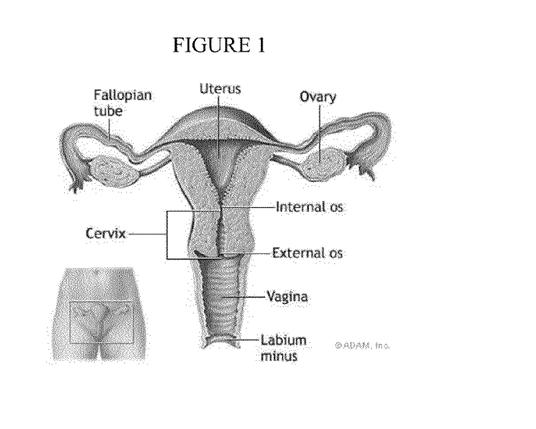
FIG. 1. Cross-section of female anatomy showing the shape of the vagina and cervix.

The vaginal vault is shown in cross section in FIG. 1, and it can be seen that it is wider at the cervix, and that the cervix has a semi-circular shape that protrudes into the vaginal vault. Thus, the prototype vaginal balloon shape mirrored this shape, being wider or flared at its distal end, which sits adjacent the cervix in use. Furthermore, since the balloon must function together with existing brachytherapy applicators, it has a hollow core into which the applicator can fit, and in most cases both ends are open, one end open for insertion of the applicator, and the other end also open, as seen in FIG. 2-5, so that the Applicator comes into direct contact with the tissue, if desired.

Although the first prototype had a significant flare (see e.g., FIG. 3-4 with 1 cm flare), reflecting the shape of the vaginal vault, subsequent tests showed that this shape was not optimal. In the original large flare design, the vaginal walls were thus placed at varying distances from the applicator, and doctors reported that this complicated and interfered with dosimetry. Therefore, two subsequent designs were prepared instead. In the first design, the balloon lacked a flare (see e.g., the cylindrical designs of FIG. 7 or 9), and thus when inflated to fill the vaginal space, the distance between the applicator and the tissue was the same along the length of the device, facilitating delivery of a constant dose.

Figure 3A:
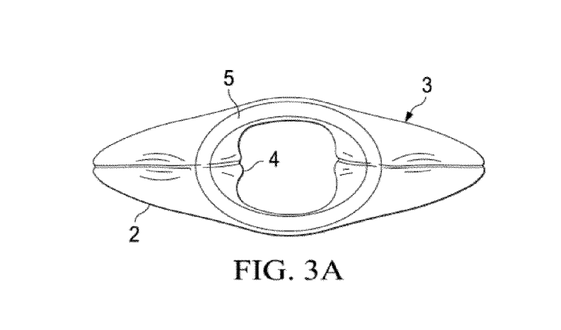
FIG. 3A-B. Top view of brachytherapy balloon shown unconstrained (A) and constrained (B). Under constraint, the 2× flare is squeezed on the sides and bulges on the top and bottom making the balloon radially symmetrical.
Figure 3B:
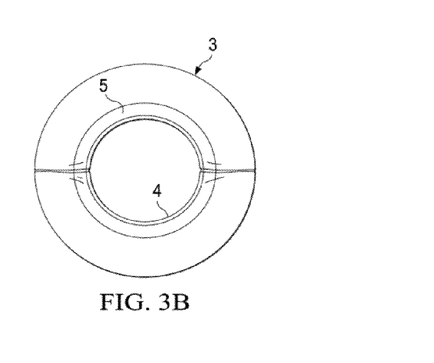

In a second design, a small flare of about 2 mm was provided at the distal end (see e.g., FIG. 3, but with reduced flare size), a such design is useful for patients with a hysterectomy, which can leave a small void, thus the small flare at distal end serves to fill the apex of the vaginal vault.

Thus, the balloon is generally toroidal in shape, although the toroid is elongated to accommodate the length of the applicator. The inner side of the toroid is cylindrical to fit adjacent a cylindrical applicator, and the outer side is shaped to accommodate the bodily orifice of interest. Thus, the outer layer can be flared, uniform or cylindrical, or welds can be created between the inner and outer layers of the balloon to create a dimple or groove, e.g., into which a prostate might fit.

To prevent the applicator from pushing past the open distal end, the distal end also has a "retention ring" designed to sit against the cervix, and hold the applicator. The retention ring is slightly smaller than the diameter of the applicator and serves to prevent the applicator from sliding all the way beyond the balloon tip. The retention ring can be made in any number of ways. The retention ring can be an O-ring, or a ring of additional material can be welded to the balloon, or the very distal end can be rolled (as in a prophylactic) or folded back and welded, or the two layers welded together at that end, or a layer of less stretchy adhesive can be added thereto, or the material at the end can simply lack sufficient stretch, so that the applicator cannot pass the retention ring.

In place of the retention ring, it is also possible to cover the end of the balloon with a layer of balloon material, the thin layer preventing the applicator from protruding past the balloon, and contributing little to distance for the diseased tissue.

The balloon shape is conforming, that is it holds a reproducible shape even when constrained by the anatomy. Thus, the balloon is flexible, and can adapt to changing anatomy, but the basic shape is retained even when vaginally constrained as in FIG. 4.

The balloon is of course fitted with means for introducing air or other fluid such as water or contrast, and keeping the fluid therein, and these can be of any shape or design known in the art. Typical means for introducing fluids can be a lumen or flexible tube with stopcock or other valve means and connector for fluidly connecting to a syringe or other air or fluid source. Alternatively, a luer lock can be used in place of a stock cock and luer connector.

The universal balloon has been tested and functions to ensure perfectly reproducible positioning of the applicator on each use. Further, the balloon is inflated to ensure a good custom fit on each patient, appropriate spacing between the applicator and the tissue, and removal of air pockets. Since the balloon is inflatable, it will expand to tightly hold even the smallest applicators for a given application.

Figure 6:
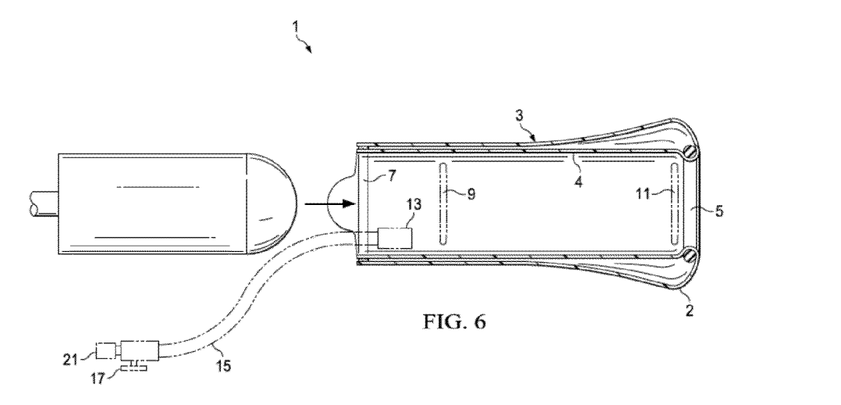
FIG. 6. Balloon in cross section.

Different shapes and/or length of outer surfaces are possible, and one example is seen in FIG. 6, which may provide a better shape for a more cylindrical cavity, such as the rectum. Cylinders, bulges, flares and indentations can be provided as needed for the body cavity in question.

The balloon can also be provided with a groove, as described in U.S. Ser. No. 12/034,470 and related cases (incorporated by reference herein). In such case, a portion of the outer surface of the toroidal balloon can be welded to the inner surface, e.g., along a oval or rectangular area appropriately located along the length of the balloon, thus creating a dimple or depressed wedge into which e.g., the prostate can be wedged.

The balloon can also be advantageously provided with a second lumen that travels the length of the device and provides a passageway for the escape of gas and such embodiment is beneficial for a rectal balloon. Ideally, such lumen might be somewhat flattened to provide minimal profile against the applicator, and has a smooth, soft tip with multiple holes for gas entry, and is positioned against the inner surface of the balloon, e.g., glued or welded thereto, although other positions and shapes are possible.

The universal brachytherapy balloon can also comprise radio-opaque markers that can be used in imaging for accurate placement of the balloon, and could also comprise passive radiation sensors, such as is used in radiation badges, plastic scintillating detectors or MOSFET sensor. Electronic or active radiation sensors can also be used, but will contribute significantly to expense, and may be less appropriate for a disposable balloon. Other sensors, such as electromagnetic motion sensors, temperature sensors, pressure sensors oxygen sensors, pH sensors, and the like can be added.

Imaging opaque markers, such as dense metals or radioactive materials or radiopaque markers, can be letters indicating top (T) or right (R) and left (L) sides of the balloon, or numbers or any other shape, and can be particularly advantageous for those balloons whose shape is not radially symmetrical. An end marker can also be placed on the very tip of a gas lumen, if included therein, or a marker can be placed at the very end of a balloon wherein the distal end is covered, or two, three, or four equispaced markers can be placed at or near the retention ring in an open ended balloon.

Dose planning and delivery is also designed to mimic the vaginal vault anatomy. For treatment of the upper vagina (two-thirds to one-third), a flared dose distribution with a tapered tail extending to the lower third of the vagina may be suitable because this is where the target treatment zone is, and the balloon design as described herein keeps the applicator centered and immobilized, and it is more comfortable with the tapered tail. However, a uniform dosage along the length may be preferred instead, and this is provided by a cylindrical balloon exterior.

In one embodiment, the universal brachytherapy balloon has a cylindrical inner surface, said inner surface defining an interior hollow of diameter D with one open end or two open ends into which a separate brachytherapy applicator of diameter $x \leq D$ can fit, an outer surface shaped to fit a body cavity; said inner and outer surface defining an inflatable elongated toroidal shape having a distal and a proximal end; said distal end having constriction or portion having a diameter less than x (if x is 0, the end is not open, but closed), and the constricted portion in most cases having a retention ring; and a closable means for introducing a fluid into said balloon to inflate said balloon.

There are several clinical advantages of the balloon sheath design herein. The system eliminates air gaps. The system provides increased comfort through the ability to use a smaller applicator with the system. The system allows for a reduction in prescription dose, so that the PTV equals the CTV, and thus has potential to reduce toxicity. The system immobilizes and centers the applicator, so that there is no need to change the angle and position is constant. The balloon is preferably polyurethane because it does not stick to the vaginal lining and is thus more comfortable.

The elongated toroidal balloon of the invention is the first of its kind, allowing a single balloon that can fits over a customers existing single- or multi-channel applicators, and not being designed and/or manufactured as part of a single applicator or to fit a single applicator. The balloon fills the space in the body cavity, ensure that the distance between the radiation source and the tissue is predictable. For example, the surface of vagina tissue is ridged and variable and use of the applicator alone often results in air pockets that receive less dosage.

However, insertion of e.g., a multi-channel applicator into a cylindrical balloon, insertion of both into the vagina, and inflation of the balloon will push the vaginal tissue a constant 1-4 mm (as desired based on the inflation level) from the applicator, allowing accurate dosing of the affected tissue. Further, the same balloon can ensure a uniform dosage, regardless of patient variability in size and/or topology, because balloon size varies in part depending on the amount of fill. The balloon is made with a moderately stretchy material and allows a small degree of size variation depending on the amount of fill, and small, medium and large sizes can easily be provided for selection and use.

The balloon can be air or water or saline filled as desired by the practitioner. When liquid filled, the balloon provides a uniform bolus that surrounds the applicator, and the size of the bolus can be varied by controlling the amount of overfill and thus stretching of the material. Bolus has been defined as "a specifically shaped material, which is usually tissue equivalent, that is normally placed either in direct contact with the patient's skin surface, close to the patient's skin surface, or inside a body cavity. This material is designed to provide extra scattering or energy degradation of the beam. Its purpose is usually to shape the dose distribution to conform to the target volume and/or to provide a more uniform dose inside the target volume".

The balloon described herein can act as a bolus by providing homogeneity during treatment planning and delivery. The presence of the customizable, tissue equivalent, water filled device replaces the transient gas volumes with a consistent and reproducible volume. Effective treatment planning can be achieved and a consistent dose delivery is assured with the presence of the device.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim. The phrase "consisting of" excludes additional elements, and the term "consisting essentially of" excludes material elements, but allows the inclusion of nonmaterial elements, such as labels, instructions for use, radio-opaque markers, stoppers, and the like.

The following abbreviations are used herein:

| | |
|---|---|
| HRD | High radiation dose |
| VBT | Vaginal brachytherapy |
| PTV | Planning target volume |
| CTV | Clinical target volume |

DESCRIPTION OF EMBODIMENTS OF THE INVENTION

The manufacture of conforming brachytherapy balloons is not a simple task. It is insufficient to merely make a mold of the desired shape, and pour latex over it. No matter the shape, it will be largely lost when such a balloon is overinflated or squeezed, especially when the applicator fits inside the balloon, rather than inside an interior hollow that is not in fluid communication with the balloon.

The prior art balloons are made in this way, with the applicator sealed inside the balloon, which is then inflated (e.g., U.S. Pat. No. 7,338,430, US2009227827, US2008293994, US2010185173, US2010048978). This provides for a difficult (and probably not sterile) seal unless the applicator and balloon are sold as a single unit, which makes the device considerably more expensive. It also provides more elastic material for stretching and deforming under pressure and contributes to the non-conforming nature of such balloons.

Another solution to the non-conforming balloon problem, was to provide two balloons, one on each side of the applicator (US20100145132). This is a viable solution, but means that two fluid filling means have to be provided, and still allows the applicator to slip out from between the two balloons. The dual balloon system is also difficult to use unless sold together with the applicator as a single integrated unit. The added complexities of separate balloon chambers, and the integration with the applicator, both serve to make this device more expensive.

Yet another solution was to provide integral balloon applicator devices with nested inner and outer balloons (US2006020156, US2010069878). Again, the device is complex and cannot be universally used with existing applicators since the balloon structure is integrated with the applicator structure. Obviously, such as device is also expensive to manufacture.

To address these unmet needs, we have provided a toroidal balloon with a hollow cavity into which the applicator can be fitted (like putting a finger in the hole of a donut) without communicating with the inflated interior of the balloon. Thus, the balloon has a complex topology, having an interior enclosed volume that can be inflated, yet also having a hollow space (or tube or cavity) into which a cylindrical applicator can be positioned.

Toroidal balloons already exist, e.g., US2010010287, but these are more complex structures and are integrated with an applicator, rather than being universal. US2008086083 in contrast is a simple donut shape, but made by a complex helical wrapping mechanism, and thus difficult to manufacture. Furthermore, the donut will not engage an entire applicator, and there is no mechanism to prevent the donut from moving along the applicator.

The elongated toroidal balloon of the invention comprises two sides. The inside is shaped to fit over a cylindrical shape of the applicator with both ends open. The outer side is flared at the distal end to fit into the vaginal vault or otherwise shaped to be consistent with the body cavity of interest. A lumen and stopcock or other means are provided to inflate the balloon with water or contrast or other fill content, after the applicator has been fitted thereinto, and the device positioned in a patient.

A ring of increased structural support and/or decreased diameter (e.g., smaller than the diameter of most applicators) is optionally provided at the distal end, and the applicator abuts against this "retention ring" while in use. The retention ring functions to prevent the applicator from protruding past the distal end of the balloon, as happened with early prototypes, and it also serves to prevent the balloon from inverting on removal.

In the first prototypes, the retention ring was an O-ring, but it also can be any additional support structure or material on the distal end of the balloon that prevents the flexible balloon from stretching and prevents the applicator from protruding through the opening. Thus, the O-ring can be replaced with a ring of less flexible material, glued or otherwise welded to the distal end of the balloon, or a string, or cable, a raised ridge, or circular weld, or the end covered completely, provided only that that it prevents stretch and/or otherwise serves the applicator retention function.

Currently preferred prototypes eliminate the O-ring, but shape the balloon to be smaller in diameter at the distal end, so that most applicators cannot pass through the small opening provided, and a circular weld added to make a less flexible retention ring. The preferred size of the opening is thus about 2-3 cm, or more preferred about 2.5 cm for a vaginal applicator. Obviously, balloons for other applications can be of different size.

In some embodiments, the O-ring thickness can be varied so as to provide a distance -d- that the applicator is held away from tissue, but often it is preferred to allow the applicator to directly contact the tissue. In preferred embodiments the O-ring is welded into position inside the balloon, as this is more structurally stable and the balloon material provides a protective and smooth covering. The weld to hold the O-ring in position need not completely circumnavigate the balloon, but can be two or more spot welds, and this weld may be optional, where the balloon has a slight notch into which the O ring fits.

Preferably the balloon material is an elastomeric polymer. The universal balloon can be made in two layers that are welded to form the correct shape. For example, two shaped lengths of flat film are welded along their sides to form a tube, which is then folded back on itself, and welded at the bottom (proximal) end. As yet another alternative, the balloon can be dip molded or blow molded as a shaped tube, the closed end (if any) clipped, and the tube folded back on its self, and thus the side welds omitted. Alternatively, the mold itself can be toroidal, thus avoiding the inverting step.

By "weld" herein we mean any method of attaching two layers of polymer film together. Thus, the welds or attachment points can be heat welded, RF welded, ultrasound welded, glued, solvent welded, hot gas welded, freehand welded, speed tip welded, extrusion welded, contact welded, hot plate welded, high frequency welded, injection welded, friction welded, spin welded, laser welded or any other means known in the art.

The balloon is preferably made of thermoplastic elastomers (TPE), especially thermoplastic polyurethane. Other balloon fabrication materials include latex, polyethylene (PE), polyprolyene (PP), silicone, vinyl, polyvinyl chloride (PVC), low density polyethylene (LDPE), polyvinylidene chloride (PVDC), linear low density polyethylene (LLDPE), polyisobutene (PIB), and poly[ethylene-vinylacetate] (EVA) copolymers, nitrile, neoprene, and the like. It is also possible to use a laminar plastic, having more than layer, e.g., a tougher interior layer and a biocompatible and/or slippery outer layer.

The ideal material is a translucent, biocompatible material, that can be sterilized, has durometer Shore 40 A to 75 D, preferably less than 80-100 Shore A (ASTM D2240 or ISO 868), a tensile strength of at least 1000 psi, 2000 psi, or more preferably 3000 psi (ISO 527-3 or ASTM D882-02), a reversible elongation stretch of at least 150%, 200%, 300%, an elongation at break of at least 200%, 300%, 400%, and that is air tight even under 150% stretch. Where the O-ring is omitted, the retention ring distal portion of the balloon should have minimal stretch under usage conditions, preferably <5%, <2% or <1% stretch under normal use.

One preferred material is an ether based thermoplastic polyurethane of 70-100 Shore A, preferably 80-90 Shore A Durometer hardness, and a thickness of 0.003-0.015 inch. This material shows outstanding abrasion and wear resistance, superior toughness and durability, yet allows ease of processing and manufacturing flexibility. It also has a nice surface feel that allows the balloon to easily slide into the body. Additionally, polyurethane is manufactured without the use of plasticizers, which means it will retain its original performance characteristics for longer time periods. Not having plasticizers also means it will not leach out hazardous compounds, which is of particular importance for medical uses.

When the device is welded, at least the outer layer is preferably inverted so as to put the welds, which can be stiff or sharp, on the inside of the balloon. Furthermore, if welded from 2 pieces, rather than being molded in a 3D shape, the flare should be about twice the flare of the corresponding cavity (assuming that the cavity is radially symmetrical). In this way, under the pressure of the constrained environment of the body, the flare will be compressed in the side-to-side axis, and instead bulge in the front-to-back axis, thus providing an annular flare that is about radially equal.

The balloon is welded at the proximal end, so as to provide an air tight enclosure and a closable means for introducing a fluid into said balloon is also provided. This can be an access lumen with stopcock or other valve means and fluid supply connector means such as a luer lock or connector or rubber gasket through which fill content is injected. Fluid introducing means can be added at any stage, e.g., to the flat film, welded tube or final balloon shape, as convenient for manufacture.

A secondary weld near the proximal end is also preferable, as this prevents the tube from continually rolling on itself as the applicator is inserted. Depending on the construction methods, the balloon can also be welded at the top (distal end) and along the sides.

In another embodiment, the material is dip molded, as is typical with an latex balloon, but one end is cut off and the tube is folded back on itself to create the double layers with interior open ended hollow. The balloon is welded at the proximal end, and a retention ring added to the distal end. Where a separate retention ring is placed at the distal end, the balloon can be spot welded to hold the ring in place. This embodiment may be preferred because fewer welds reduces the cost of manufacture.

In yet another embodiment, the inner layer can be molded or unitary, and the outer layer welded along the periphery. In yet another embodiment, two shaped tubes can be welded at the top and the bottom. In yet another embodiment, the mold can be toroidal, and if needed to remove the balloon from the mold, the weld can be at the flared end for ease of removal from the mold. The choice of how to implement the toroidal balloon is based on manufacturing and material costs balanced against the number of units predicted, and as can be seen, many variations are possible.

We have described in some detail herein a vaginal brachytherapy balloon, but the shape of the balloon is easily adapted to other body cavities, as illustrated in the figures below. Thus, the brachytherapy balloon can be used to treat a variety of tissues, such as the rectum.

Ether based thermoplastic polyurethane pellets were obtained and melt blown film of 0.003-0.015 inch thick was prepared. The actual performance characteristics were as follows:

|  | Test Values | Test Method ASTM |
|---|---|---|
| Durometer | 84A | D2240 |
| Specific Gravity | 1.1 | D792 |
| Elongation @ Break Elast | 660% | D412 |
| Tensile Str. @ Break Elast | 3,800 psi | D412 |
| 100% Modulus | 750 psi | D412 |
| 300% Modulus | 1,150 psi | D412 |
| Tear Strength (pli) | 450 | D624 |

Figure 5A:
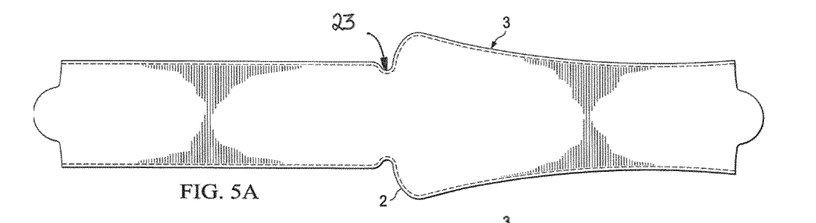
FIG. 5A-C. Manufacturing steps for toroidal balloon made with flat film.
Figure 5B:
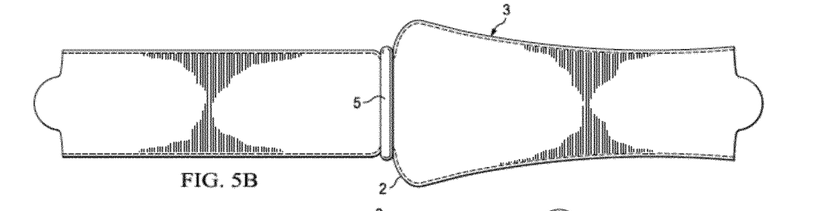
Figure 5C:
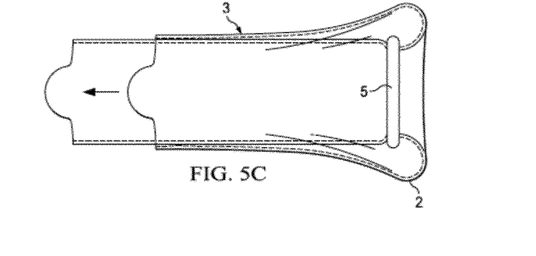

The films for making balloon 3 were cut to shape, as shown in FIG. 5. It can be seen that the desired shape is rectangular on one half, and the other half mirrors the body shape, albeit upside down of its completed shape so that flare 2 is adjacent the O-ring. An optional notch or indent 23 can be included midway, and this serves to hold the O-ring in position at the distal end of the balloon.

The two long sides of the two pieces of film were heat welded using RF or dielectric welding along the edges (see dotted line). A medical grade silicone O-ring 5 was fitted over the tube and came to rest about midway, where the small indentation 23 was provided to hold the O-ring. Next, the tube was folded back over the O-ring and the bottom ends welded shut at weld 7 (not shown in FIG. 5, but see FIG. 2). Thus, the side welds were now inside the balloon. One or more spot welds 11 holds the retention ring 5 in place, if needed, and secondary weld 9, can help prevent the tube from rolling along its length, which it is prone to do without a secondary weld.

Figure 2:
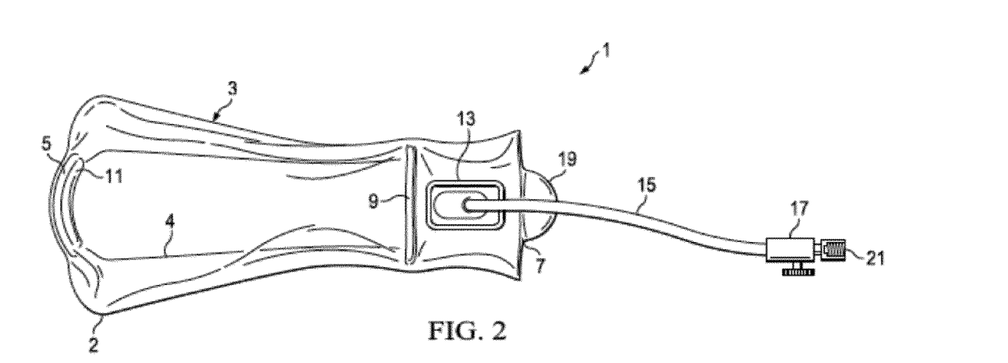
FIG. 2. Top view of universal brachytherapy balloon design to fit in the vagina and having a flared distal end and tapered tail.
Figure 4:
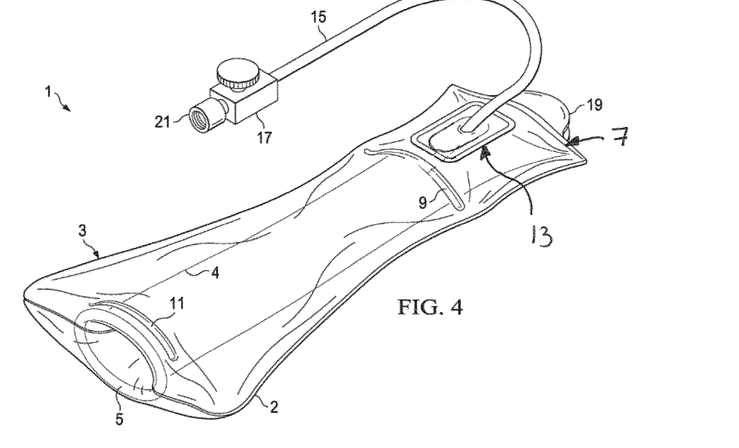
FIG. 4 Perspective view of the universal brachytherapy balloon with flared end.

The completed balloon is shown in FIGS. 2 and 4. A low profile dog house 13 on balloon 3 was added to provide a fluidic connection to a lumen or flexible tube 15, which is fitted with a valve means 17, such as a stop cock, and preferably fitted with a syringe connecting means 21, such as a luer connector. These components can be added to the film, the tube or the welded balloon, but it may be easier to add these pieces to the flat film before assembly begins. In the prototype, tube 15 was Tygon medical tubing of ⅛-¼ inch diameter in our prototypes, the valving means 17 was an off the shelf stop cock and a standard luer connector was used as an interface 21 for the air source, in this case a 100 ml syringe.

FIG. 6 shows the balloon in cross section through the middle. The universal brachytherapy balloon 1 has an elongated toroidal balloon 3 with an inner side 4 and an outer side 2, which in this case is flared at the distal end 2, but can be any desired shape. O-ring 5 is positioned at the distal end of the balloon and one or more spot welds 11 hold it in place. The retention ring 5 serves to prevent expansion of the balloon at this end and contributes to the conforming nature of the balloon. The balloon is welded or otherwise sealed at or near the proximal end at weld 7, and preferably has a secondary weld 9 some distance distal to the proximal weld 7. Weld 9 can be one or more spot welds and should not circumnavigate the balloon so as to prevent fluid communication with the rest of the balloon, although retention ring weld 11 can circumnavigate the balloon if sufficiently close to the retention ring 5. Weld 11 can also be one or more spot welds, or can be omitted entirely.

FIG. 6 also shows the dotted outlines of the doghouse 13, lumen 15, stop-cock 17 and luer lock 21, out of plane in this cross section. FIG. 2 also shows the applicator, which fits into the donut hole or interior hollow of the toroidal balloon (see arrow).

The interior hollow defined by the inner surface of the balloon has a diameter D that is as big as the largest applicator for a particular indication, and the retention ring has a diameter less than D that is smaller than the smallest applicator (or any external sleeve on said applicator). In use, the balloon inflates to tightly juxtapose even the smallest applicator. Thus, balloons of a particular shape and size can fit all standard applicators for a particular application, e.g., cervical cancer, and different balloons can be provided for different applications, e.g., prostate cancer or esophageal cancer. Further, device can be used with single channel applicators, or multichannel applicators fitted with obturator sleeves (an external cylinder or sleeve housing the multi channel applicator).

FIG. 4 shows a top view of the universal brachytherapy balloon 1, with toroidal balloon 3 having a cylindrical inner side 4 and a flared outer side 2, wherein the flare is at the distal end in a vaginal balloon, but whose shape can be modified according to the intended use. Welds 7, 9, 11 are shown, as well as retention ring 5. Also shown are optional pull tabs 19 at the proximal ends that assist the practitioner in inserting the applicator. The toroidal balloon 3 is fitted to a lumen 15, in this case via a low profile doghouse 13, and the lumen fitted with valve means 17 for containing the air pressure on inflation, and optional syringe connecting means 21.

The end of the toroidal balloon is shown in FIGS. 3A and 3B. In FIG. 3A the balloon is unconstrained, as it would be outside of the body. However, when inflated inside the vaginal vault, the constraints applied by the vagina shape the balloon into a circular shape in cross section, giving equal spacing between the applicator and the tissue in all 360 degrees. This, unique and desirable characteristic is a result of the flared shape of the original layers of film, wherein the flat 2D flare was about twice the cross section flare of the vaginal vault. Thus, the 2D shape can be converted to a radially symmetrical 3D shape, by making flares and bulges about twice as big as needed in cross section.

Figure 7:
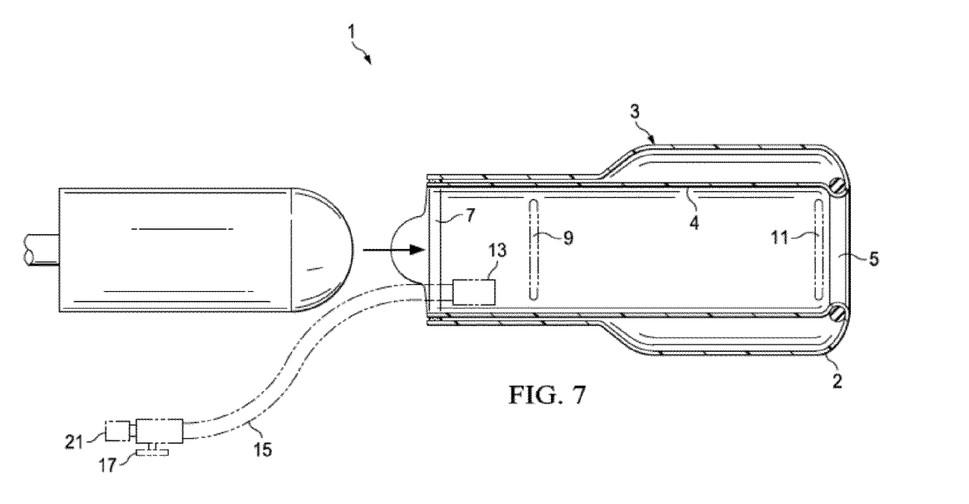
FIG. 7. Alternatively shaped balloon.

A different shape outer surface 22 is shown in FIG. 7, which may provide a better shape for a more cylindrical cavity, such as the rectum. Cylinders, bulges, flares and indentations can be provided as needed for the body cavity in question.

Finally, the balloon is vacuum evacuated, sterilized if needed, e.g., by gamma irradiation, ethylene oxide sterilization, low-temperature hydrogen peroxide gas plasma, autoclave, and the like, and packaged for sale.

Figure 8A:
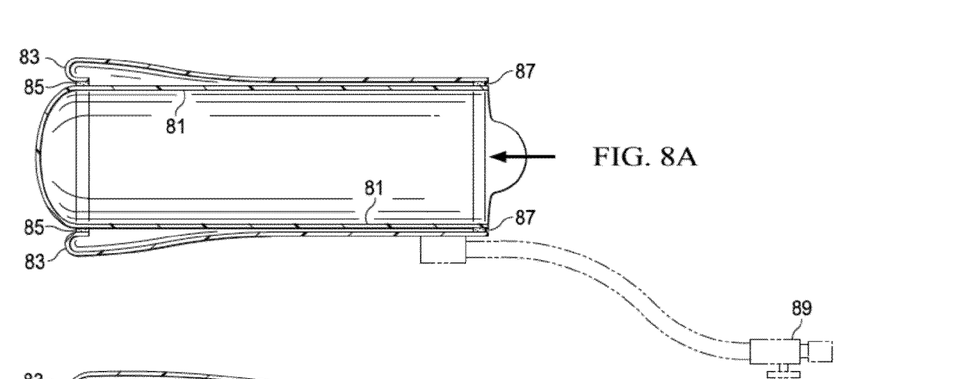
FIG. 8A. Cross-section of another embodiment of the balloon having a covered end.

Another embodiment of the balloon is made in this example and shown in FIG. 8. An inner tube with closed distal end 81 is made by dipping a closed tubular form into a suitable polymer or by welding two layers together on each side and the top or by folding and welding a rectangular sheet on one edge and the top. Inner layer 81 is thus shaped like a traditional prophylactic and the cylindrical shaped interior can receive a cylindrical brachytherapy applicator.

The outer layer 83 is also tube shaped, but somewhat longer than the inner tube. The outer layer can be welded 85 to the inner layer just shy of the distal end, using e.g., a circular heated welding wire and a tubular jig to hold the components in place. The proximal ends also welded 87 shut and filling means 89 added thereto. The circular weld at the distal end is sized to comfortably cup the cervix and is about 1-3 cm, preferably about 2 cm from one side to the other.

Figure 8B:
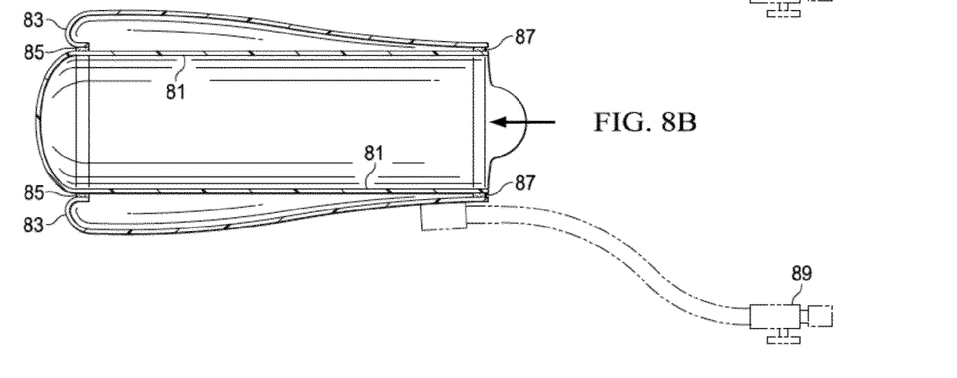
FIG. 8B. Cross-section of balloon of FIG. 8A when inflated.

When inflated (FIG. 8B) inside the vaginal vault, this design will produce a distally flared balloon with cylindrical hollow, wherein the end of the applicator is covered by a single layer of plastic film, and wherein the outer layer creates a dimple into which the cervix can fit. If desired, the outer layer can alternatively cover the distal end, or both layers can cover the distal end, but the arrangement in FIG. 8 is preferred as easier to manufacture. However, a covered distal end may be preferred where sterile equipment is needed since the balloon can be sterilized for use, and prevent direct contact of the applicator with any tissue.

If preferred for ease of manufacturing, both the inner and outer layers can cover the end of the applicator, such that the radiation must pass through two layers of film, although it is possible to remove or omit one or both of the layers at the distal end.

In this embodiment, the applicator never touches the patient, being completely enclosed by the inner balloon. This embodiment may be preferred as helping to avoid the transfer of infectious agents between uses. Further, the outer tube is simply cylindrical in shape, and the flare comes from the slight excess in length of the outer tube. Thus, this embodiment is very conserving of materials, especially if the other tube is made by welding a rectangular strip along one edge and preferably inverted so the edge weld in on the inside of the resulting balloon.

The above described brachytherapy balloon has been made and tested. The practitioner inserts either a single- or multi-channel applicator into the interior hollow of the toroidal balloon, using optional pull tabs to assist with the insertion. In contrast to what has been previously recommended, the smallest diameter applicator can be used, since the balloon fills all of the voids and naturally conforms to individual anatomy. The applicator with balloon sheath is inserted into the body cavity of the patient, a syringe fitted to the luer lock, and the balloon inflated with a fluid, such as air, water, saline or other fluid, preferably water or aqueous contrast, until the applicator is wedged into the cavity. The practitioner is advised to note how much fluid is injected into the balloon, as using the same amount will ensure consistency from treatment to treatment.

Our investigations to date show that the retention ring, toroidal balloon shape, flared outer shape and secondary weld, all serve to ensure perfect positioning each time the vaginal balloon device is used. Thus, the conforming universal balloon allows reproducible positioning on every use.

Another prototype has been developed that omits the O-ring, and instead uses the pattern of FIG. 5*a*, but with significantly less flare. The two layers of plastic material are cut to shape, welded together along the sides, and turned inside out or folded back at constriction 23. A circular weld is applied at constriction 23, welded the two layers together. This weld thus functions as the retention ring. This design is even simpler to manufacture, and costs less in materials since O-ring 5 is replaced with a welded retention ring.

Figure 9A:
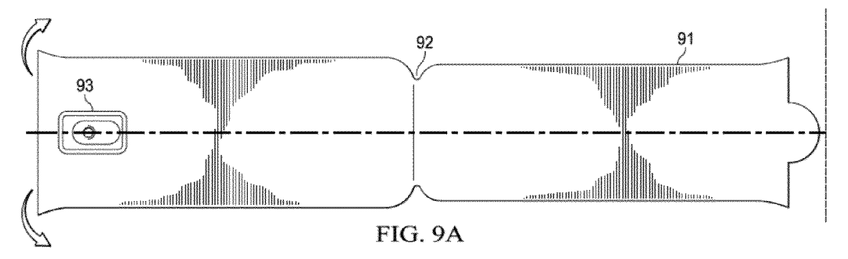
FIG. 9A. Pattern for a cylindrical brachytherapy balloon, showing welds in FIG. 9B and inflated to form a cylinder in FIG. 9C.

Yet another prototype has been developed in FIG. 9 that omits the O-ring, and instead uses the pattern of FIG. 5*a*, but with out flare (e.g., similar to FIG. 7), thus making a cylindrical balloon shape. Two layers of plastic material are cut to shape per the outline shown as 91. The two layers are welded together along the sides (not shown), and turned inside out or folded back until reaching constriction 92 (see arrows in FIG. 9A). A low profile lumen connector or port 93 can be added at any time, but may conveniently added before this initial weld.

The outer portion of the balloon (left side here) should be at least as big or bigger (wider) than the right hand portion, which will provide the inner surface of the balloon. For example the left hand portion is about 1-2 mm wider than the right hand portion, allowing 1-4 mm space between the layers when the balloon is inflated, depending on how much it is inflated and how much stretch there is in the material. The difference can be made greater if more space is desired on inflation.

Figure 9B:
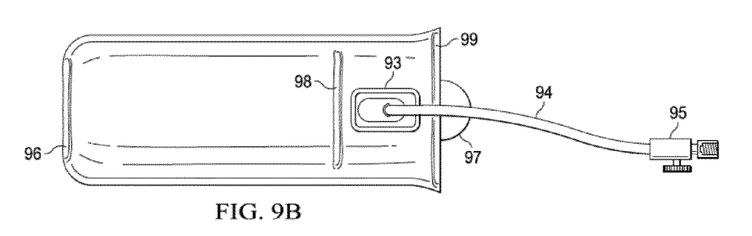
Figure 9C:
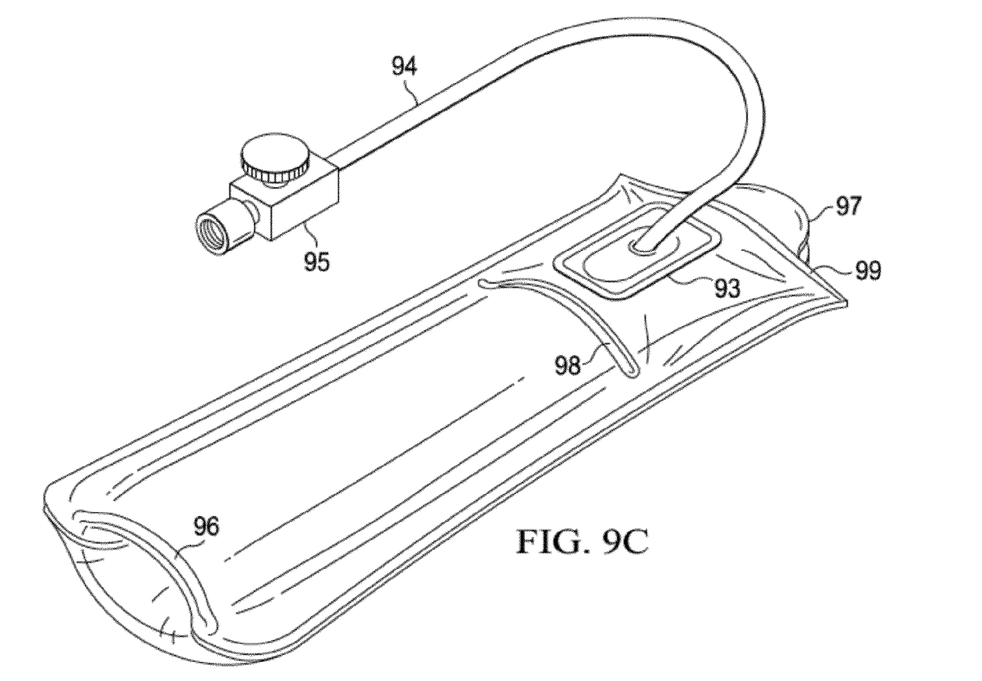

Once folded back, a circular weld 96 is applied at constriction 92, welding the two layers together. This weld 96 thus functions as the retention ring, and can completely circumnavigate the balloon or preferably partial openings can be left at the side welds, thus minimizing bulk at the side welds. This design is even simpler to manufacture, and costs less in materials since O-ring 5 is replaced with a welded retention ring. Also shown are pull tab 97, which makes it easier to pull the completed balloon over the applicator. Lumen 94 and stop cock 95 are also shown, as is partial weld 98 and a complete (airtight) weld 99 at the base of the balloon.

The foregoing disclosure and description of the invention is illustrative and explanatory thereof. Various changes in the details of the illustrated construction can be made within the scope of the present claims without departing from the true spirit of the invention. The present invention should only be limited by the following claims and their legal equivalents.

What is claimed is:

1. A brachytherapy balloon system, comprising a brachytherapy applicator and a brachytherapy balloon, said brachytherapy balloon adapted to fit a vagina, a rectum or an oesophagus and being made of elastomeric polymer and having: a) a cylindrical inner surface, said inner surface defining an interior hollow of diameter D with at least one open end into which said brachytherapy applicator of diameter $x \leq D$ can fit, b) an outer surface; c) said inner and outer surfaces defining an inflatable elongated toroidal shape having a distal end and a proximal end; d) said distal end having a diameter less than x; e) a closable means for introducing a fluid into said brachytherapy balloon to inflate said brachytherapy balloon; and f) a retention ring at said distal end of said brachytherapy balloon that prevents said brachytherapy applicator from protruding beyond said retention ring.

2. The brachytherapy balloon system of claim 1, wherein said interior hollow has two open ends.

3. The brachytherapy balloon system of claim 1, wherein said retention ring is a weld between said inner surface and said outer surface.

4. The brachytherapy balloon system of claim 1, comprising a weld connecting said inner surface to said outer surface between said proximal and said distal ends.

5. The brachytherapy balloon system of claim 1, wherein said retention ring is an O-ring inside said brachytherapy balloon at said distal end of said brachytherapy balloon and further comprising a weld connecting said inner surface to said outer surface adjacent and proximal to said O-ring, and a secondary weld connecting said inner surface to said outer surface between said proximal and said distal ends.

6. The brachytherapy balloon system of claim 1, wherein said retention ring is a retention ring weld between said inner surface and said outer surface at said distal end of said brachytherapy balloon, and further comprising a secondary weld connecting said inner surface to said outer surface between said proximal and said distal ends.

7. The brachytherapy balloon system of claim 1, wherein said outer surface of said brachytherapy balloon is cylindrical.

8. The brachytherapy balloon system of claim 1, further comprising an opaque marker that can be imaged.

9. The brachytherapy balloon system of claim 1, further comprising a passive radiation sensor.

10. The brachytherapy balloon system of claim 1, further comprising an active radiation sensor.

11. The brachytherapy balloon system of claim 1, further comprising an electromagnetic motion sensor.

12. The brachytherapy balloon system of claim 1, further comprising a gas lumen that allows the passage of external gas or fluid from beyond the distal end to beyond the proximal end.

13. The brachytherapy balloon system of claim 1, wherein said closable means for introducing a fluid into said balloon is a lumen fitted with a valve means and a connector for a fluid supply.

14. The brachytherapy balloon system of claim 1, wherein said closable means for introducing a fluid into said balloon is a lumen fitted with i) a stopcock and luer connector, or ii) a luer lock.

15. The brachytherapy balloon system of claim 1, wherein the brachytherapy balloon is made of thermoplastic polyurethane.

16. The brachytherapy balloon system of claim 1, wherein the brachytherapy balloon is made of thermoplastic polyurethane and is welded shut at said proximal end and has a weld between said proximal and distal ends connecting said inner and outer surfaces.

17. The brachytherapy balloon system of claim 1, wherein the brachytherapy balloon is translucent.

18. The brachytherapy balloon system of claim 1, wherein the brachytherapy balloon is made of translucent thermoplastic polyurethane having a 80-100 Shore A durometer, a tensile strength of at least 3000 psi; and 100% modulus of 500-1000 psi.

19. A method of contact brachytherapy treatment comprising inserting said brachytherapy applicator of claim 1 into said brachytherapy balloon of claim 1, inserting said brachytherapy balloon and brachytherapy applicator into a vagina, a rectum or an oesophagus of a patient, inflating said brachytherapy balloon, and providing brachytherapy radiation to said patient via said brachytherapy applicator.

\* \* \* \* \*